(12) United States Patent
Simbruner et al.

(10) Patent No.: US 6,228,106 B1
(45) Date of Patent: May 8, 2001

(54) THERMAL SUIT FOR A PREMATURE BABY

(76) Inventors: Georg Simbruner, Lindwurmstrasse 4, D-80337 Munchen (DE); Torsten Frankenberger, Uhlandstrasse 37, D-40237 Dusseldorf (DE)

(*) Notice: Subject to any disclaimer, the term of this patent is extended or adjusted under 35 U.S.C. 154(b) by 0 days.

(21) Appl. No.: 08/985,460

(22) Filed: Dec. 5, 1997

Related U.S. Application Data

(63) Continuation-in-part of application No. 08/945,147, filed as application No. PCT/DE96/00681 on Apr. 18, 1996, now abandoned.

(30) Foreign Application Priority Data

Apr. 19, 1995 (DE) .............................................. 195 14 387

(51) Int. Cl.[7] .................................................... A61F 7/00
(52) U.S. Cl. .................................. 607/96; 607/104; 2/69
(58) Field of Search ...................... 128/873, 846; 2/69; 607/96, 104, 108, 109

(56) References Cited

U.S. PATENT DOCUMENTS

| | | | |
|---|---|---|---|
| 3,908,655 | * 9/1975 | Lund | 128/256 |
| 4,404,460 | * 9/1983 | Kerr | 219/211 |
| 4,691,762 | * 9/1987 | Elkins et al. | 165/46 |
| 5,755,756 | * 5/1998 | Freedman, Jr. et al. | 607/110 |
| 5,891,187 | * 4/1999 | Winthrop et al. | 607/96 |
| 5,928,274 | * 7/1999 | Augustine | 607/107 |

* cited by examiner

Primary Examiner—Linda C. M. Dvorak
Assistant Examiner—Jocelyn Debra Ram
(74) Attorney, Agent, or Firm—Jacox, Meckstroth & Jenkins

(57) ABSTRACT

The garment is intended for an infant and especially a newborn infant and surrounds at least the trunk. Its inside is made of material tolerated by the skin and is impermeable to water vapor, at least from the inside outwards. The garment leaves the child's face free and, in those regions where a point on or part of the body remains open, has sealing means to seal the garment against the body. The garment is heat-insulating and intended for use inside and outside the incubator. One embodiment includes a climate controlled infant suit for independently regulating the climate (such as temperature, humidity and the like) associated with an infant's head and/or body. The suit includes a cover for covering at least a portion of the head and/or body and a climate control coupled to said cover for independently controlling the climate associated with the head and/or body so that the infant's head temperature may be kept below a predetermined temperature, as well as below the infant's body temperature. The suit may include a helmet and a body suit and the helmet may have an open face or have a lid for providing a closed-faced helmet. The suit may also include a collector, such as a bag, for collecting water evaporation from the infant for purposes of measuring water loss.

28 Claims, 6 Drawing Sheets

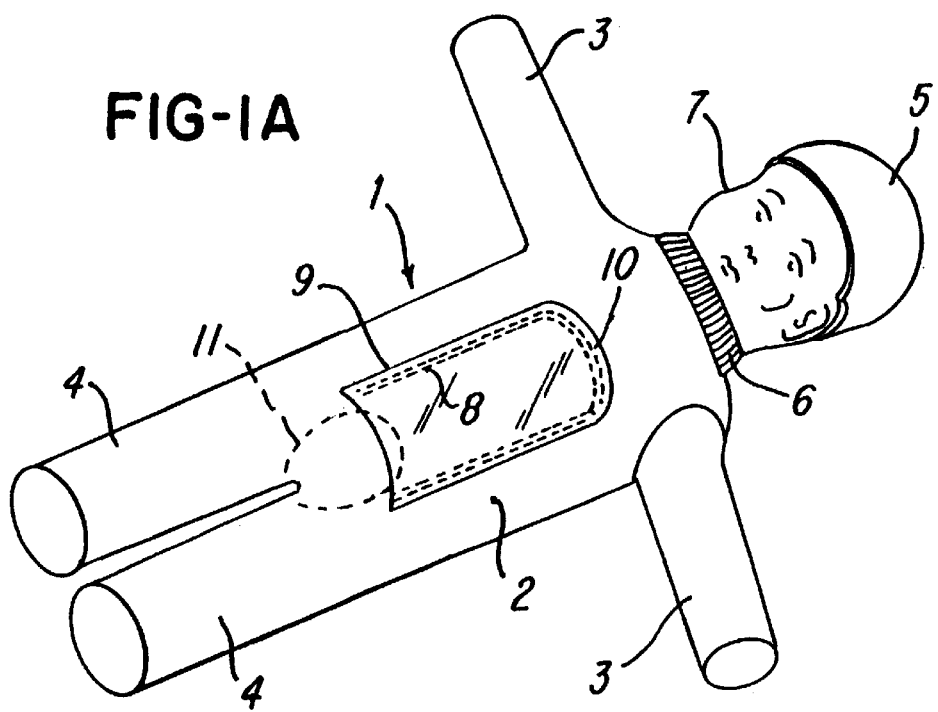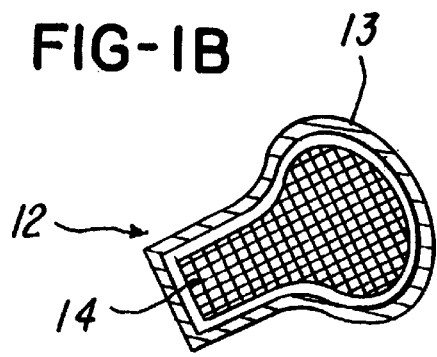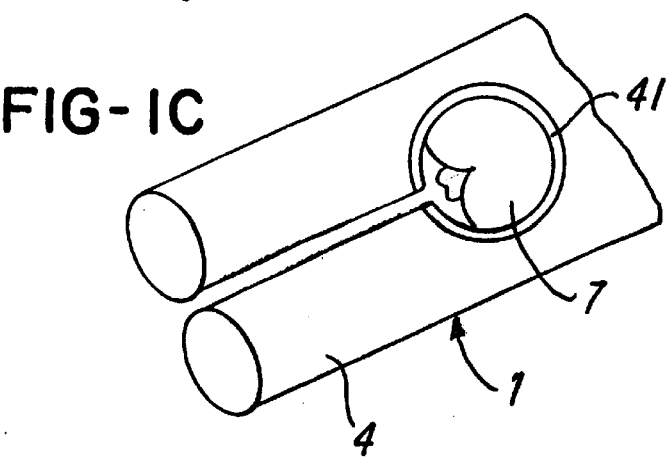

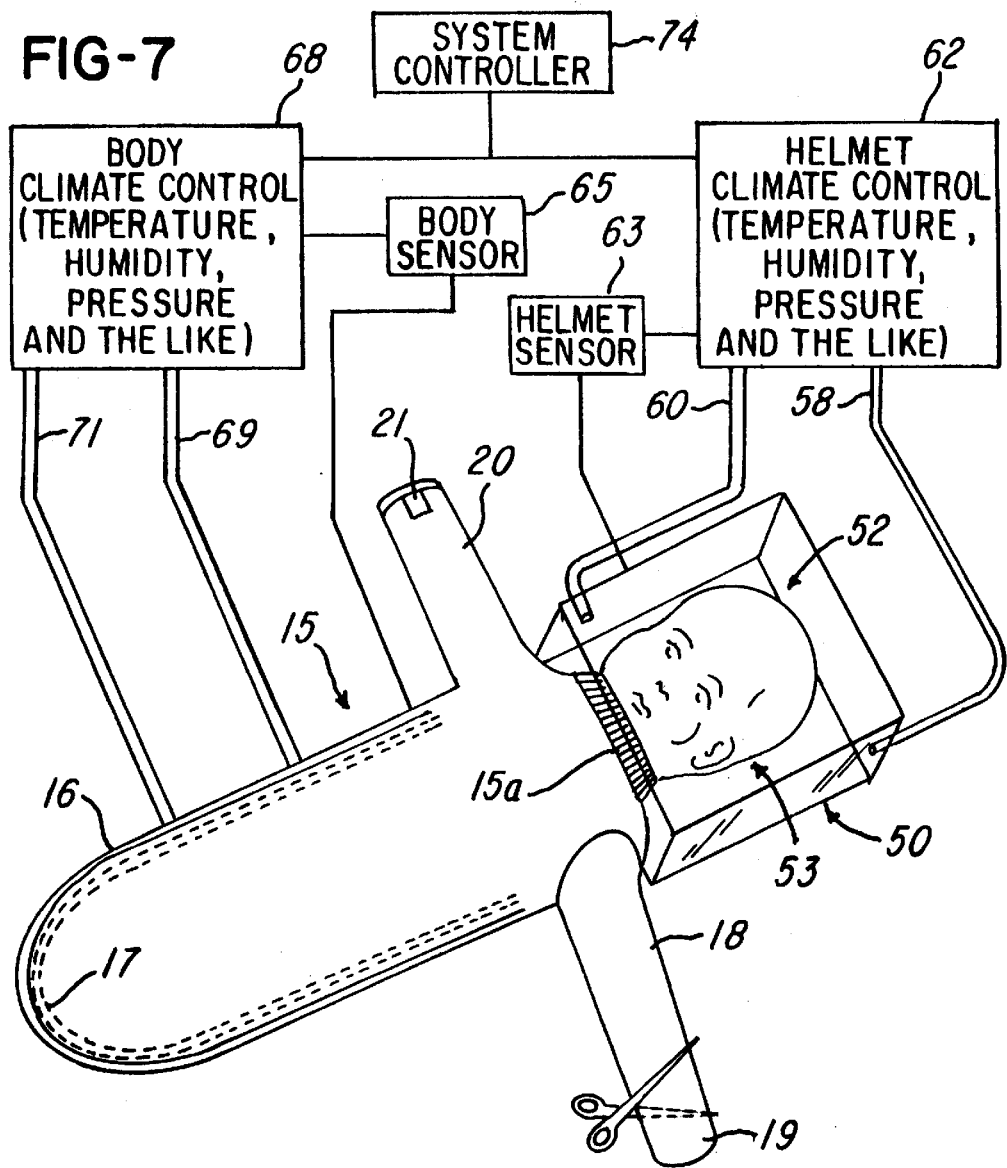
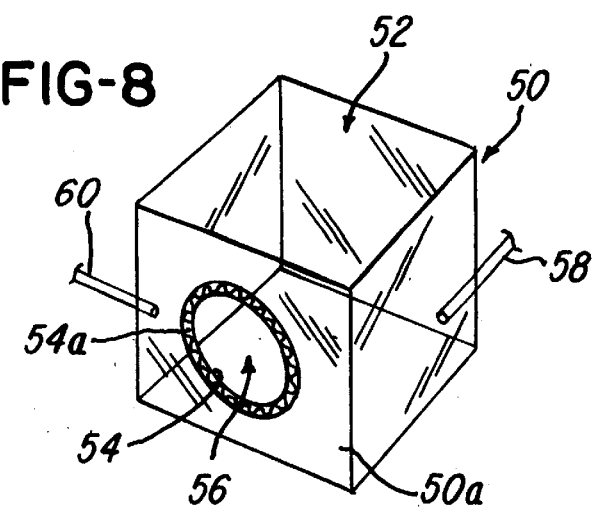

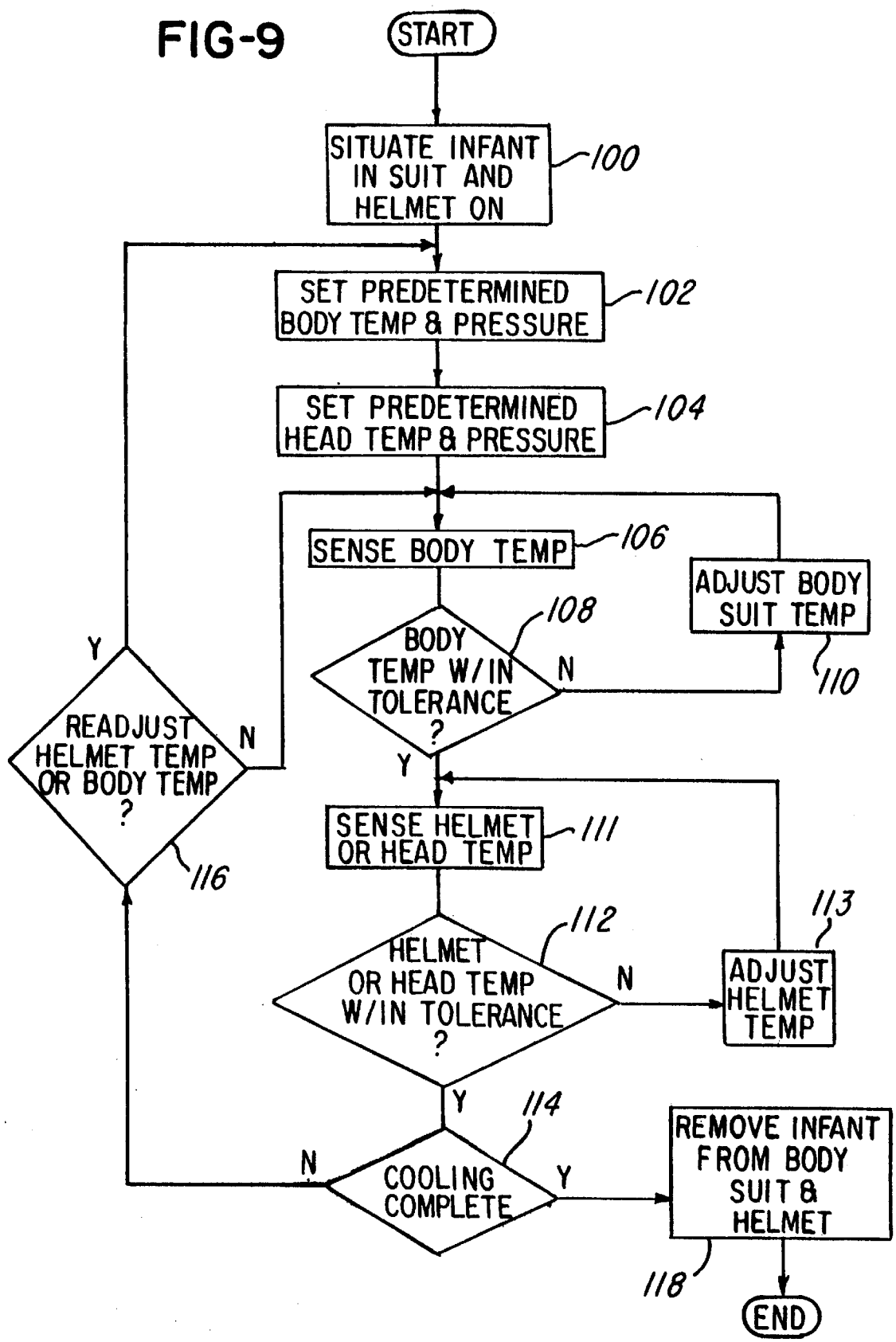

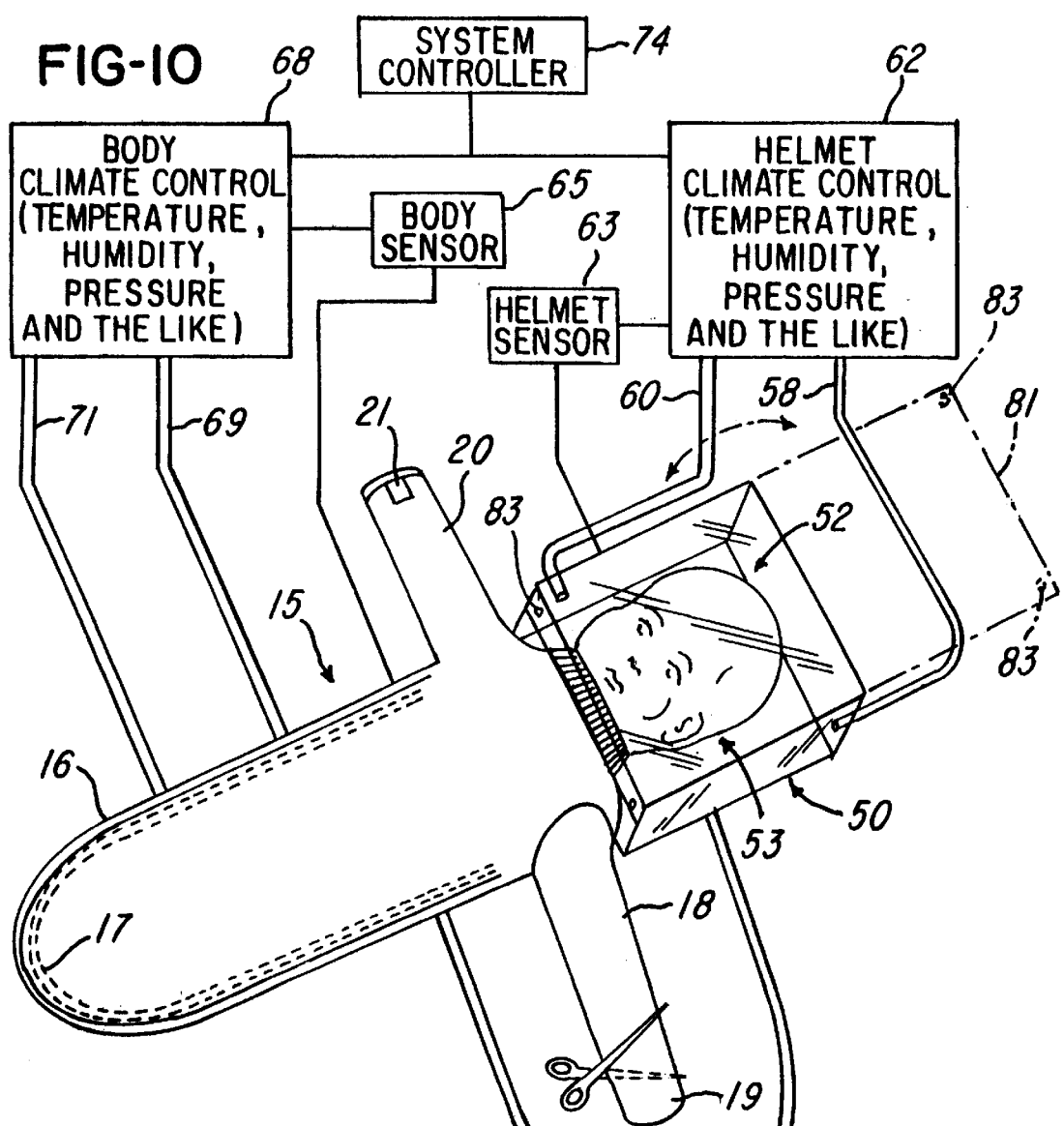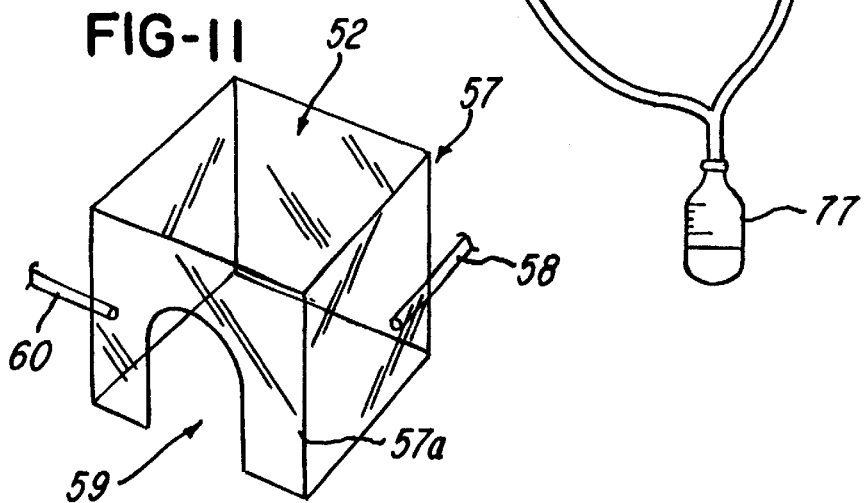

THERMAL SUIT FOR A PREMATURE BABY

RELATED APPLICATION

This application is a continuation-in-part application of Ser. No. 08/945,147 filed Jan. 15, 1998 ABN, which is a national stage application of PCT/DE96/00681 filed Apr. 18, 1996.

BACKGROUND OF THE INVENTION

This invention relates to a suit for an infant, in particular, a newborn infant.

In particular with premature infants it is often necessary to protect them from the free atmosphere with regard to temperature, humidity and oxygen content and to provide an artificial atmosphere which makes the survival of the infant easier and aids the maturing process. Such an atmosphere is nowadays attempted to be produced in incubators. Such incubators are generally manufactured of transparent material. With regard to size they are dimensioned such that they may not only accommodate the infant as such, but the infant may also be handled within the case, and for this appropriate handling openings are provided. In order to keep the atmosphere within this formation within predetermined limits with regard to temperature, humidity and oxygen content, these being particularly required for the development of the infant, appropriate supply units with controls and likewise are provided. Such systems are known in numerous embodiments and are for example described in DE 36 16 359 A1.

A disadvantage with these comparatively large spacial formations is that an exact heat balancing is not possible. It is, however, desirable since the premature infant may only direct all energy into its growth in a thermoneutral maintaining environment. Furthermore, it is seen as disadvantageous that a rapid temperature control, as is desirable from a therapeutic point of view be it for reducing or increasing the body temperature, is hardly possible due to the large masses of air.

Even more difficult is the balancing of fluid economy which with incubators at present is not possible at all. It is however important to know how much water the infant needs in order to replace as completely as possible the loss of fluid via the skin, the excretions and in the breath. Since the balancing of the fluid economy of the infant in the incubator is at present not possible, one has already gone over to increasing the air dampness in the incubator up to the saturation limit in order to minimize fluid loss via the skin and breath. This however brings with it considerable disadvantages, with regard to the water supply as well as removal. The water vapor condenses on the walls of the incubator, which on the one hand leads to the view into the incubator no longer being possible or at least being much hindered, and on the other hand leads to there forming locations at which water collects, this not able to be removed or only with difficulty. Since the dampness in combination with the heat produces good conditions for the formation of germs, exacting in this region with high air humidity, there arises problems during operation as well as cleaning.

Although in the meantime there are transportable incubators on the market, the infant however for the purpose of transport must always be transferred to another incubator, which brings with it irritations. Moreover the transportable incubators too are very bulky, such that the infant also therein can only be transported in a limited manner.

Also small heating beds are also know, these being provided with mattress heating and/or with a heat irradiator from above. As a complementary measure, a sheet cover is known from U.S. Pat. No. 4,712,263.

One conventional approach to controlling the infant's body temperature is the use of the incubator. Some of the downfalls of incubators are that opening the incubator causes the temperature and water vapor to fall for a certain period of time. An increase of humidity to above 80% sometimes results in condensation and invisibility of the infant. Although incubators are mobile to some extent, infants have to be taken out for a ride in a transport incubator, for radial logic investigations, like magnetic resonance imaging (MRI).

Another problem with incubators is that neither radiologic nor surgical interventions are possible under a constant, homogeneous, humid environment. The incubator with its large gas capacity in the matters with its large heat sink prevent rapid and proportional regulation of environment. Also, incubators offer no means to assess water loss to guide fluid intake and replacement.

There is scientific evidence that has proven that mild brain hyperthermia, for example, 2°–3° higher than normal, aggravates morbidity and neuronal damage. In contrast, mild hypothermia, lowering the temperature for example 2–3° C. below normal, has been shown to protect against neuronal damage in case of ischemic-hypoxic insults to the brain. It has been found that lowering of brain temperature of levels which are protective for neuronal damage facilitates improving the neurological and thus psycho-motor developmental outcome. Thus, it has been suggested that a thermal environment which fosters not only healthy growth, but also protects against squele of brain injury is desired.

Moreover, incubators provide the same environment for the head and its brain as well as for the rest of the body. Since the brain temperature provides a decisive roll for neural damages after hypoxic insults, differentiated regulation of head temperatures and protective hypothermia is a protective, therapeutic goal which cannot be achieved by the incubator as such. High temperature in incubators and, in particular, heated mattresses might even be dangerous to a hypoxic brain.

In the past, plastic foils or polyurethane patches, covering the infant, have been employed to minimize the water loss. Heated mattresses have been provided, but they provide heat homogeneously. Unfortunately, none of the aforementioned devices have offered a satisfying solution to selectively and independently controlling an infant's head temperature versus body temperature so that, for example, the head temperature can be lowered while the body temperature is kept at a normal temperature.

There is, therefore, a need to provide a system and method for independently and selectively controlling an infant's head temperature and body temperature.

SUMMARY OF THE INVENTION

Against this state of the art, is the object of the present invention to remedy the disadvantages outlined above or at least to reduce them, and this being with technically simple means.

According to the invention, for this a suit for an infant, in particular a newborn infant is put forward, which comprises the features specified in claim 1. Advantageous further formations are indicated in the dependent claims as well as in the following description.

The invention envisages a suit which at least encloses the body rump of the infant and on the inner side consists of non-irritant material. The suit is impermeable to water vapor at least from the inside to the outside, in order to reduce fluid loss via the skin to a large extent. Furthermore the suit is designed to be thermally regulated, and where a body location or body part remains free and the suit would comprise an opening to the atmosphere, is sealed with respect to the body by way of a sealing connection in order to reliably separate the inner and outer atmosphere of the suit.

The suit according to the invention is applied in conventional incubators, but may also be applied outside of the incubator, for example for the purpose of transport but also for the purpose of examination. Thus a multitude of radiological examinations, such as for example nuclear spintomography, but also other diagnostic methods may be applied, without having to remove the infant from the suit. The infant thus always remains in its protective atmosphere which is ensured by the suit.

Preferably the suit is designed such that it leaves free the face of the infant and only this region, so that he mouth and nose remain accessible for the purpose of breathing and intake of food, and so that the condition of the infant may be ascertained at all times by way of observing the face. Where appropriate for this facial region there may be provided a protective shield which additionally also protects the face from heat loss and in particular may serve to prepare an increased oxygen concentration of the inhalation air or to enable a tubus and its connecting tubings to be reliably fixed in this region. Such a shield may for example be displaceably arranged on a helmet belonging to the suit. With this it is essential that the protective shield can be quickly removed and that when permitting, the view into the facial region remains free.

The design construction of such a suit may vary considerably with regard to shape and choice of material, preferably at present the construction of such a suit is of plastic sheeting, which may be cheaply manufactured as a disposable product.

The suit according to the invention may in its simplest form be designed sack-like, wherein only in the neck region should there be provided a suitable connection to the body of the infant. Preferably however tubular parts in the suit are also provided for the arms and legs, which are however formed noticeably longer than the extremities of the infant. Preferably with this, these tubular parts are formed closed at the free ends, but they may however also be provided with Velcro-type fastening (trademark), adhesive or other closures on the end side. With a closed design, when the access to an extremity is required, the closed end is cut open and in this manner access is provided. This open end may then be closed again by folding or with the help of an adhesive tape or other closures on an end side. In this manner the impermeability of the suit in these regions is ensured in the simplest manner, but the access is however retained.

On the rear side of the suit preferably a flat and closable opening should be provided, via which the excretions of the infant may be quickly and simply removed. This opening should be either formed such that through this a fleece or nappy located in the suit may be removed or replaced, or also such that the region of the anus and where appropriate the genital region is relieved, and which by way of a fleece-covered sheet may be covered and sealingly closed. In order to prevent excrement from getting into the inside of the suit, the suit is preferably provided with a peripheral adhesive tape provided on the inner side of the opening. By way of this the body region in which excretions are effected is more or less shifted out of the suit into a separate chamber which may be covered over by a fleece-coated sheet. This sheet part formed as a cover for the opening, with a fleece lying thereunder, forms a hygiene part which may be handled as a disposable nappy, i.e. when required may be quickly and simply replaced without having to irritate the atmosphere prevailing in the remaining suit.

Appropriately, on the front side a closable, large-surface opening should be provided so that the breast and the belly of the infant are quickly accessible without having to take off the suit. This may for example be required for the purpose of auscultation of for ultrasound examinations on the body. Where appropriate still further closable and again sealable openings may be provided in the suit or when required be produced in order to lead sensor cables, drainages or likewise to the outside or to make certain locations of the body accessible.

The thermal insulation of the suit may on the one hand be ensured by an appropriate choice of materials, preferable however the suit is manufactured of plastic sheet in such a manner that within the suit air chambers are formed which form an insulating pad. The suit thus consists then of one or more air chamber which form an insulating pad.

According to a preferred further form of the invention, the suit is not only designed thermally insulating but furthermore is also designed such that the climate within the suit with regard to the temperature and where appropriate also with regard to the air dampness may be controlled. For this the suit is designed such that fluid can flow through it. This may be effected in an indirect manner (only temperature control) in that similar to the previously described pads, the suit is passed through by a channel system through which fluid either in the form of gas or in the form of liquids (water down to 0° C. and alcohol below 0° C.) can flow. This channel system may completely or partly replace the previously mentioned air pad. An even quicker temperature control may on the other hand be achieved in that the suit, for the purpose of temperature regulation and/or for the control of the air dampness, is designed so that fluid either in the form of gas or in the form of liquids (water down to 0° C. and alcohol below 0° C.) can directly flow through it. Then at least a fluid entry and exit are provided. In order to achieve a uniform through-flow with a small as possible flow speed, a central fluid entry and fluid exit may be provided via the extremity tubes. Further, one or more outlet connection pieces preferably in the region of the tubular leg parts may be provided via which the urine can be drained.

In the neck region the suit is usefully equipped with a collar which permits a tight as possible bearing on the neck but on the other hand leaves free the required neck cross section for the unhindered breathing. A directed control of the neck pressure of such a sleeve may be provided in the form of an annular sleeve which can be impinged by fluid either in the form of gas or in the form of liquids (water down to 0° C. and alcohol below 0° C.), whereby the bearing force may be set via the fluid pressure. Practical tests have shown that is already sufficient to form the suit in this region similar to a polo-neck, thus with excess material in the neck region which where appropriate may be fixed on the body with adhesive tape.

In particular with the use of textile material for the suit, one must keep an eye on the impermeability to germs. As has been previously mentioned, germs admitted into the damp warm atmosphere of the suit represent a danger potential.

Since a large part of the body surface (about one quarter) with a baby is taken up by the surface of the head, it is desirable to cover a large part of this head surface also with the suit. On the one hand this may be effected by a hood formed on the suit which merely leaves free the facial region of the infant (mouth, nose, eyes as well as where possible also the ears), but also, which is presently to be preferred, by a separate helmet separated from the suit.

Helmet in the context of the intervention is to be understood less in respect to a protective function but more to the function of an embodiment or cover of a head for regulating the climate around the head. This embodiment for or cover over the head may be realized either in the form of a snugly fitting helmet or a container in the form of a box-like shape not snugly fitting the head. Both forms of head embodiments are fitted with thermoregulatory devices, preferably to regulate the climate around the head and brain, respectively.

In order to reliably fix the helmet on the head of the infant, inner lying chambers which are fluid fillable may be provided which via an appropriate control of filling pressure come to bear on the head of the infant with a defined force. With a less expensive alternative, foam material pads are provided within the helmet on oppositely lying sides, with which the helmet supports itself on the head of the infant.

Preferably the helmet consists of an outer, essentially dimensionally stable shell, on whose inner side a large-surface arranged channel system through which fluid either in the form of gas or in the form of liquids (water down to 0° C. and alcohol below 0° C.) can flow through is provided which serves for temperature regulation. The helmet too must in any case be thermally insulating.

In the inside of the suit as well as the inside of the helmet there may be provided sensors with which body functions or operations of the infant can be monitored. This may for example be thermosensors for determining the surface temperature and heat loss of the infant, which in turn are connected to the temperature control of the suit. In the helmet region preferably EEG electrodes as well as also Doppler-sensors may be provided, or can at least be mounted.

Preferably in the upper helmet region there is provided an opening through which the ultrasound oscillator of an ultrasound diagnosis apparatus may be coupled to the head of the infant. Instead of this closable opening at this location of the helmet a recess may also be provided, in which the ultrasound coupling path, for example in the form of a gel cushion, may be incorporated. Then the ultrasound oscillator of the diagnosis apparatus may be directly applied to the upper side of the helmet.

The small inner volumes of the helmet and suit permit a very direct temperature control, so that preferably a proportional-assist-control may be applied. With the suit according to the invention, the body temperature of the infant may be increased or also reduced in a directed manner, as long as this appears to be necessary due to medical reasons, or also appears only to be useful.

Another object of the invention is to provide a system and method for independently and selectively controlling an infant's body temperature and head temperature.

Yet another object of the invention is to provide a system and method for controlling an infant's head temperature.

In one aspect, a climate controlled infant suit for independently regulating the climate of an infant's head and/or body, for use with an infant and especially a newborn infant, consists of a cover for covering at least a portion of the head and/or body and a climate control coupled to the cover for independently controlling the climate associated with the infant's head and/or body so that at least a head temperature of the infant is maintained a predetermined temperature.

In another aspect, the invention comprises an incubation system consisting of a body suit for receiving a body of an infant, a helmet for situating over a head of the infant, and means for selectively and independently controlling a temperature inside said body suit and said helmet.

In still another aspect, this invention comprises a method for selectively and independently controlling a temperature of an infant during incubation, consisting of the steps of establishing a predetermined body temperature and a predetermined head temperature for the infant, placing the infant's body in a body suit, placing a helmet over the infant's head, selectively controlling the temperature inside said body suit and helmet such that an actual body temperature and actual head temperature are within a predetermined tolerance range of said predetermined body temperature and predetermined head temperature, respectively.

In another aspect this invention comprises a helmet for a baby, in particular for a premature baby, through which fluid either in the form of gas or in the form of liquids (water down to 0° C. and alcohol below 0° C.) can flow for the purpose of temperature regulation.

Other objects and advantages of the invention will be apparent from the following description, the accompanying drawings and the appended claims.

The invention is hereinafter described in more detail by way of embodiment examples shown in the drawings. These are shown in a much simplified schematic representation.

BRIEF DESCRIPTION OF THE DRAWINGS

FIGS. 1A–1C is a firm embodiment of a suit according to the invention in a perspective representation with an infant located therein, as well as two representations of details in FIGS. 1B and 1C;

FIG. 7 is another embodiment of the invention showing a body portion and helmet portion with an open face;

FIG. 8 illustrates the helmet used with the embodiment of FIG. 7;

FIG. 9 illustrates a process for independently and selectively controlling an infant's head temperature and body temperature;

FIG. 10 is another embodiment of the invention showing a helmet having a flap for closing a face area; and FIG. 11 is another embodiment of the invention showing a box-shaped helmet with a slot for an infant's head.

The suit 1 represented in FIG. 1A consists of a germ, air and water impermeable multi-layered plastic sheet, which is bonded with the inclusion of air chambers which are not shown in FIG. 1A. The suit shown consists of a rump part 2, tubular arm parts 3, tubular leg parts 4 and a separate helmet 5. In FIG. 5 the helmet is shown separately and in its construction is described further below.

Figure 2:
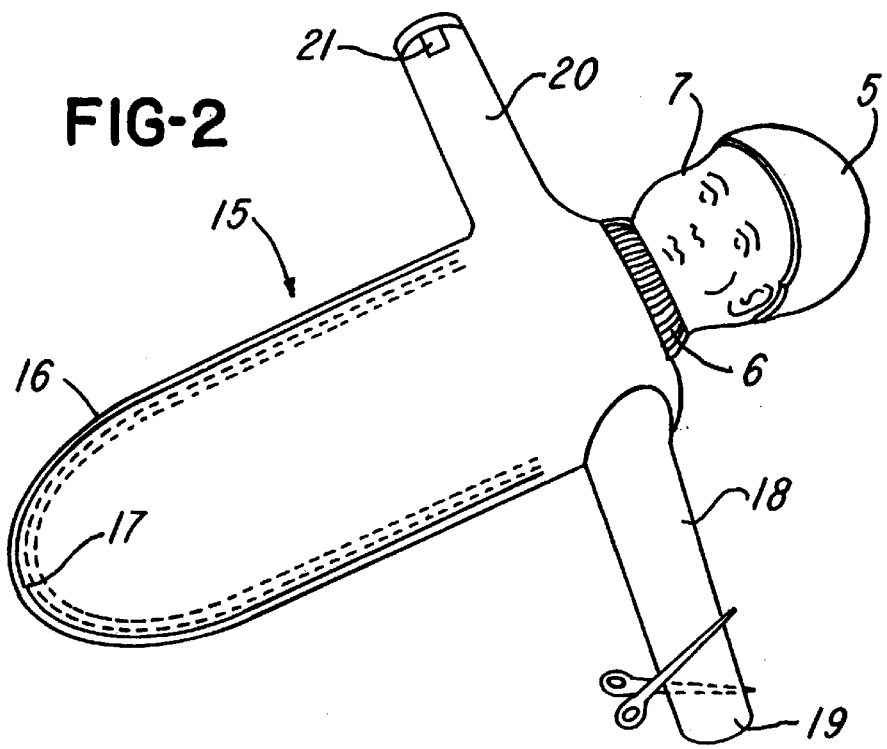
FIG. 2 is a second embodiment form in the representation according to FIGS. 1A–1C.

The arm and leg parts 3 and 4 are connected to the rump part 2, they are sealingly bonded at the free ends so that the suit 1 only in the region of its collar 6 is open. Through this collar opening 6 the infant 7 is introduced into the suit which then in the neck region sealingly contacts by way of a sleeve-like collar 6 so that the inside of the suit 1 forms an essentially closed atmosphere. The suit 1 comprises on its front side a large-surfaced recess 8 which extends from the rump up to roughly an imaginary line between the arms. This recess is covered by a flap 9 laterally projecting over the recess 8, which on its lower end is connected to the remaining suit 1 by bonding and is further releasably fastened by a peripheral Velcro-type® or adhesive connection 10 indicated in FIG. 1A. This flap 9 is transparent so that it allows a continuous visual control into the suit 1. For opening it is lifted up, then examinations on the infant may be carried out, in particular the regularly required auscultation. After examination has been effected, the flap 9 is closed by way of redoing the connection 10.

Lying opposite the recess 8, a further recess 11 is provided in the suit I on the rear side. This recess 11 encompasses at least the region of the anus of the infant, preferably 10 however also the genital region, as is represented in FIG. 1C in the detail shown below, which shows this region from the rear side. In order to prevent excretions of the infant from reaching the inside of the suit, the edge region of the recess 11 on its side facing the body is provided with a peripheral adhesive tape 41 with which this edge region may be sealingly applied on the infant. The adhesive tape 41 is indicated in the lower detail in FIG. 1C, which shows the suit in the region of this recess 11 from the rear side. This recess 11 can be closed by way of a cover 12 which is shown enlarged in the middle detail in FIG. 1B. The cover 12 likewise comprises a reversible peripheral closure in the form of a Velcro® type tape or an adhesive connection 13, with which the cover may be connected to the suit 1 at the outer edge of the recess 11. The cover 12 is designed as a hygiene part in the form of a disposable article, it comprises a fleece 14 facing the inside of the suit 1 when the cover 12 is placed on, which services the taking up of the excretions of the infant 7. When the fleece 14 is soiled by excretions, this cover is removed and replaced by a new cover 12. Since the suit is connected to the body of the infant in a sealed manner via the peripheral adhesive tape 41 in the region of the recess 11, on exchanging the cover 12 the atmosphere in the suit 1 is not disturbed. At the same time it is ensured that excretions of the infant do not get into the actual suit 1, but only in the region of this recess 11.

By way of FIG. 2, which shows a suit 15, further embodiment alternatives are represented. This suit 15 comprises instead of the leg parts 4, a common leg part 16 which blends into the rump part without seams, but which for the purpose of access to the lower extremities and to the lower rump part may be opened. For this the suit 15 in this lower part region 16 is formed as two halves forming the front and rear side, which by way of a peripheral connect 17 similar to the connections 10 and 13 in FIGS. 1A–1C, are releasably connected to one another by a VELCRO® type or adhesive closure 17. Furthermore also with this design, alternatively to the closure 17, a front and rear recess may be provided as is described by way of FIGS. 1A–1C.

As is represented by way of the left tubular arm part 18, this arm part 18 closed at its free end clearly projects beyond the length of the extremity located therein. For the purposes of access, as is shown in FIG. 2, the closed end 19 of this arm part is cut by way of a scissors. The later closure may be effected by folding or with the help of an adhesive tape 21, as is illustrated by way of the opposite lying arm part 20.

Figure 3:
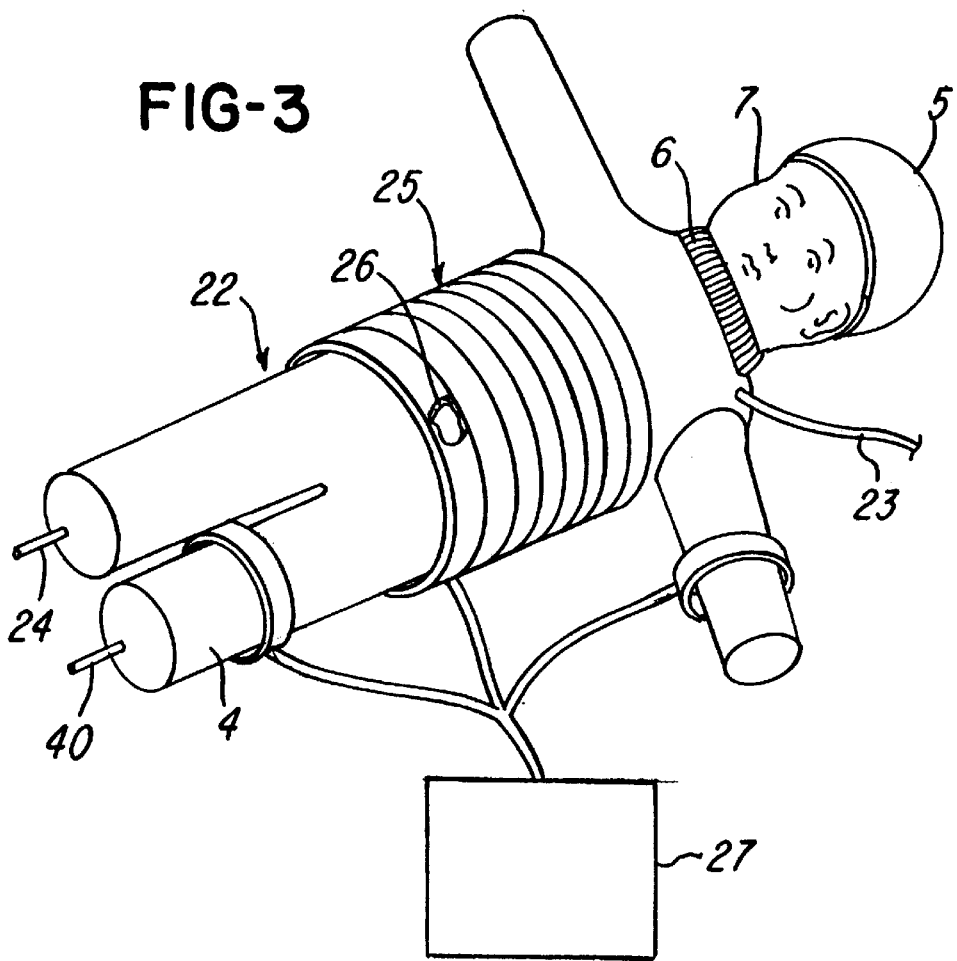
FIG. 3 is a third embodiment form in the representation according to FIGS. 1A–1C.

The suit 22 shown in FIG. 3 comprises an air entry channel 23 in the shoulder region as well as an air exit channel 24 at the free end of a leg part. As the figure shows, due to the displaced arrangement of the air entry channel 23 and the air exit channel 24, a uniform through-flow in the suit in the rump region is possible over almost the whole cross-sectional area. Via these air inlet and outlet channels 23 and 24 the air directly in contact with the infant may be replaced, circulated, purified, temperature regulated, cooled, humidity controlled or otherwise treated in a suitable manner.

Furthermore by way of FIG. 3 a suit-independent temperature regulation sleeve 25 is represented which is guided over the suit 22 with the infant located therein in the rump region. The temperature regulation sleeve 25 is connected to the suit 22 via VELCRO® type closures so that a large surfaced bearing of the suit on the temperature regulation sleeve is ensured. In this way the suit may also be lifted off the skin of the patient. The sleeve 25 comprises annular chambers 26 through which gas or also fluid can flow through and to which a suitable temperature control 27 is allocated. As FIG. 3 indicates, similar sleeve-like arrangements may be provided in the region of the leg and/or arm parts. Such a temperature regulation sleeve 25 permits a considerably more economical design of the suit 22 in comparison to a suit 1 with an integrated temperature regulation system. If the suit is specially construed for such a temperature regulation sleeve 25, a thermal insulation in the region of the temperature regulation sleeve may be omitted, so that then a temperature control may be achieved which functions just as quickly as one with a channel system integrated into the suit, but with markedly more economical manufacturing costs. This is because the complicated chamber-like system in the form of the temperature regulation sleeve 25 is reusable, only the suit 22 is foreseen as a disposable product.

Although not shown, the sleeve 25 may be integrated into suit 22, or it could be detachable from suit 22 as shown in FIG. 3.

As mentioned earlier herein, a quicker temperature control may be achieved by providing entry and exit couplings directly into the suit so that gas can directly flow through it for climate control, including controlling temperature, humidity and the like.

Furthermore the suit 22 represented by way of FIG. 3 is provided with a urine drainage connection piece 40 at the end of a leg part. Via this urine drainage connection piece 40 the urine excreted by the infant can be continuously drained.

Figure 4:
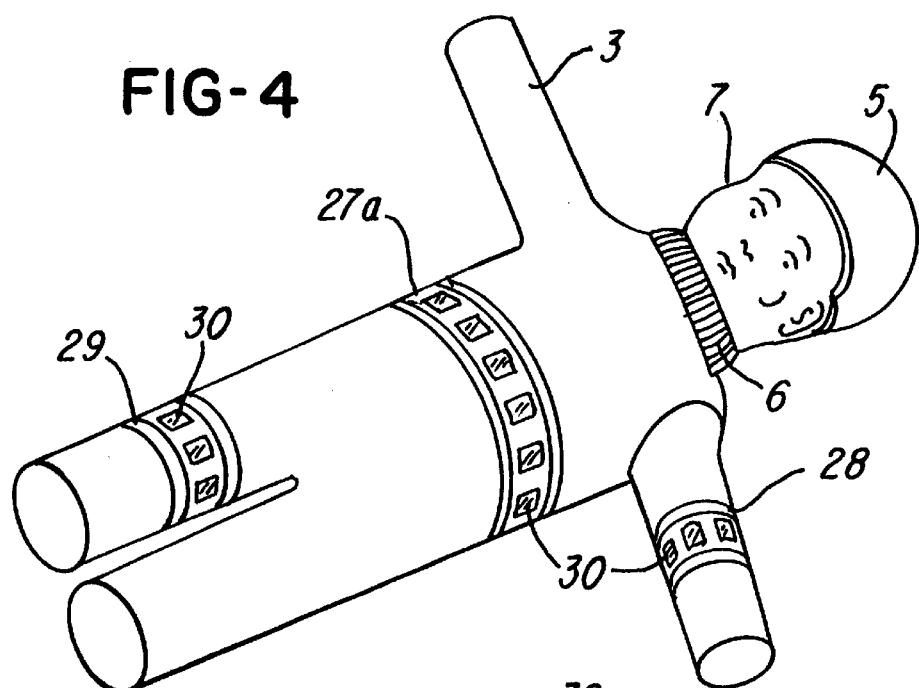
FIG. 4 is a equipping variation of the embodiment according to FIGS. 1A–1C.

By way of FIG. 4, it is shown where it is useful to arrange temperature probes 27a, 28 and 29. Thus in the rump region a tape of temperature probes 27a is provided as well as a tape 28 in the arm region and a tape 29 in the leg region. The temperature probes themselves are indicated at 30 and comprise tapes 27a outer side of the suit and may be removed and where appropriate newly equipped. The leading of the cables may be effected through the free ends of the tubular arm or leg parts of the suit or also through the collar 6.

The individual features represented in FIGS. 1A to 4 may practically be combined with one another in any way.

Figure 5:
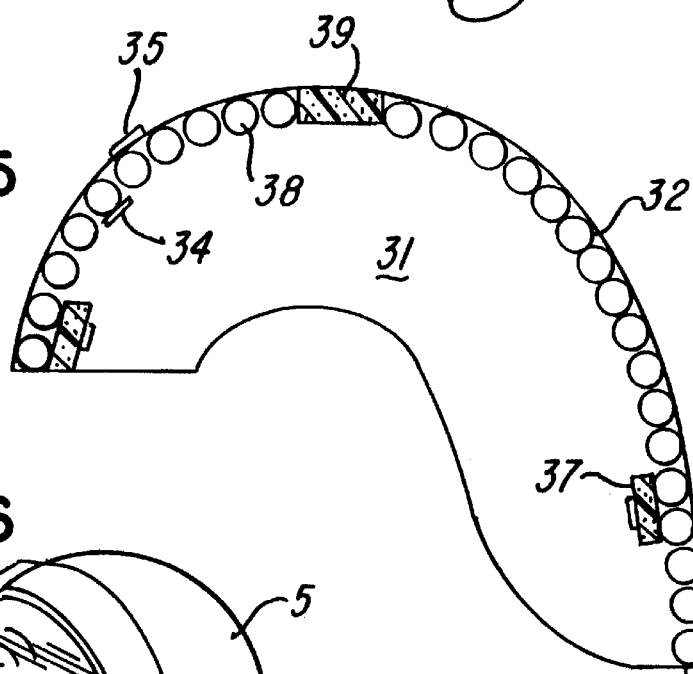
FIG. 5 is a helmet according to the invention, in longitudinal section.

The helmet 5 shown in section in FIG. 5 consists of an essentially dimensionally stable plastic shell 31, which on the inside is furnished with channels 32 in a meandering-shaped manner. The channels 32 are formed by plastic sheets bonded to one another and brought into the shape of a shell 31. The channels 32 are led out of the helmet laterally to the rear via tubings, which are not shown, in a central supply branch 33. In this supply branch 33 are also all electrical leads of the probes provided on the helmet 5. In FIG. 5 for example an EEG sensor 34 and a heat flow sensor 35 are illustrated. The supply branch 33 leads to a supply, measuring and control device 36 for the helmet and suit.

In order to fix the helmet with the required holding force and without exceeding the allowable pressure force on the head of the infant, at least three pressure pads 37 are provided which are distributed about the periphery and which in the simplest form consist of soft foam material but also alternatively are formed as pneumatic pads, which with a corresponding impingement of pressure uniformly bear on the head of the infant.

At one location of the helmet, which preferably lies over the fontanelle, there is provided a recess about the size of a Duetschmark coin the helmet shell 31 as well as in the region of the channels 32. This recess 38 is filled with a gel cushion 39 which protrudes so far on the inner side of the helmet that it bears on the scalp of the infant. In this manner with an applied helmet, through this gel cushion 39 as a coupling path, ultrasound examinations may be effected by coupling the ultrasound oscillator to the upper side of the gel cushion 39.

Figure 6:
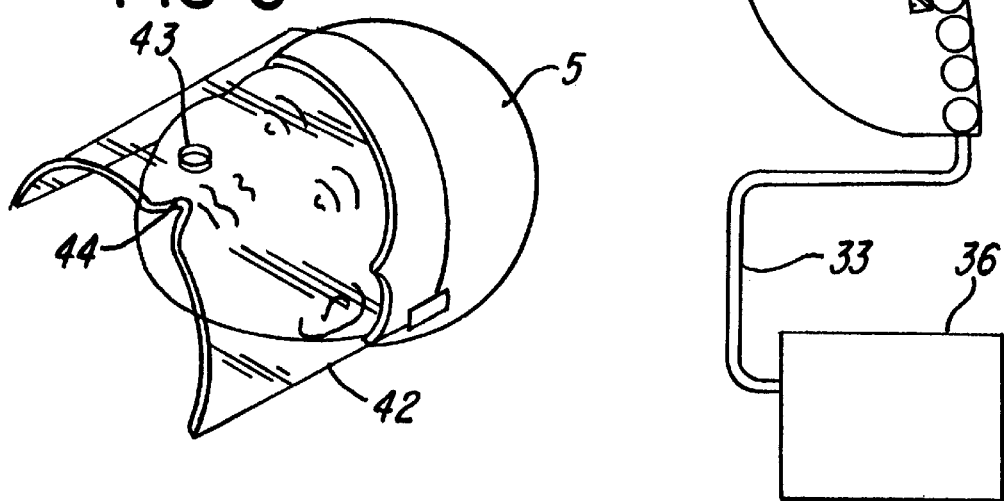
FIG. 6 is an embodiment variation of the helmet with a protective shield.

The embodiment shown by way of FIG. 6 shows a helmet 5 which is provided with a protective shield 42 which covers the facial region of the infant which is not covered by the suit and helmet. This protective shield 42 is pivotally and displaceably mounted on the helmet 5 so that it can be quickly and completely removed with a handle. The protective shield consists of transparent, essentially dimensionally stable plastic and additionally protects the facial region from heat loss. By way of this protective shield 42 is it moreover possible to make available an increased oxygen concentration of the breathing air. For this there is provided an opening 43, through which an appropriate oxygen tubing can be introduced. Finally by way of the protective shield a tubus or its connecting tubings may be fixed. For this a recess 44 on the lower edge of the protective shield 42 is provided, which comprises a clamping mechanism for fastening a tubing or likewise guided herein.

FIG. 7 illustrates another embodiment similar to the embodiment shown in FIG. 2, with like parts being labelled with the same part numbers. In the embodiment shown in FIG. 7, the suit 15 further comprises a transparent helmet 50 which defines an environment or area 52 for receiving the infant's head as illustrated in FIG. 7.

As best illustrated in FIG. 8, the helmet 50 comprises an end 50*a* having an aperture 54 which defines an opening 56 for receiving the infant's head. The aperture 54 may comprise an elastic band 54*a* integrally formed or secured to helmet SO for providing a tight seal against either the infant's neck or a collar 15*a* (FIG. 7) of suit 15. It should be appreciated, that any suitable means for securing the helmet 50 to the suit 15 may be used and such means may include, for example, VELCRO®, snaps, zippers, adhesive tape and the like. Notice in the embodiment shown in FIGS. 7 and 8 that an infant face area 53 is open to permit easy access to the infant's face, for example, for nursing or for cleaning the infant. Alternatively, FIG. 11 shows a box-shaped helmet 57 having an end 57*a* defining a slot 59 for receiving the infant's neck. This helmet 57 may be provided with or without either a top lid (not shown) or bottom floor (also not shown) if desired.

FIG. 10 illustrates another embodiment of the invention with like parts being labeled with the same part numbers. In this embodiment, notice that a lid 81 is provided which may be pivoted from an open position (shown in phantom) to a closed position (as shown). The lid 81 may have VELCRO® fasteners or snaps 83 for securing the lid 81 in the closed position.

It should also be appreciated that the helmet 50 could comprise any suitable shape for defining the environment 52 for receiving the infant's head and for maintaining a predetermined head temperature as described herein. Thus, for example, the helmet 50 could comprise a circular, elliptical, multi-sided or rectangular shape as desired.

As illustrated in FIG. 7, the helmet 50 comprises an input tube 58 for transporting a climate-controlled fluid, such as oxygen ($O_2$) gas, into environment 52 of helmet 50 and an exit tube 60 for permitting the fluid to exit the environment 52. In the embodiment being described, the tubes 58 and 60 are coupled to a helmet climate control means or helmet climate controller 62 which facilitates maintaining the climate in the environment 52 so that, for example, the temperature and humidity which the infant's head is subjected to while in environment 52 is maintained at a predetermined temperature and a predetermined helmet humidity, respectively.

The embodiment shown in FIG. 7 further comprises a body climate control 68 coupled to the body suit 15 via input tube 69 and exit tube 71 for maintaining the climate, such as body suit temperature and body suit humidity, inside the suit 15 at a predetermined body temperature and predetermined body humidity, respectively.

The embodiment shown in FIG. 7 further comprises a system controller 74 which is coupled to the body control 68 and helmet control 62 for selectively and independently controlling the climate in both the helmet 50 and suit 15. Thus, it should be appreciated that this invention provides means for selectively and independently controlling the climate in the environment 52 and inside suit 15 so, for example, that the temperature of the area 52 is held to the predetermined helmet temperature while the area or environment inside the suit 15 is held to the predetermined body temperature. This, in turn, facilitates independently controlling, regulating and maintaining the temperature of the infant's head and body, respectively.

Advantageously, this system maintains the infant's head temperature at about the predetermined helmet temperature, while the temperature of the infant's body is kept at about the predetermined body temperature, with the predetermined helmet temperature being lower than the predetermined body temperature. In the embodiment being described, the invention is capable of keeping the infant's head temperature at least 2° C. lower than the infant's body temperature. Also, a space between helmet 50 and the infant's head is of a low volume in relation to body mass (e.g., less than about 1.0 liter per Kg body mass to maintain normal valves (such as temperatures between 35°–38° C.) in a standard room at ambient room temperature). Because of this small volume, only a relatively small amount of energy, such as about 3 Watt per Kg body mass, is needed to maintain the climate inside suit 15 and helmet 50 at desired levels (such as temperatures between 35°38° C.) in a standard room at ambient room temperature). Thus, proportional-assist climate regulation which instantaneously regulates heat loss or gain according to certain various predetermined parameters (such as temperature, humidity and other factors which characterize the climate) needed to control the climate inside the environment 52.

This invention (particularly, the embodiment shown in FIG. 10), also facilitates monitoring an infant's water balance by permitting all water evaporating from the infant to be collected and measured. The collected water, along with the infant's urine losses, provide an accurate measure of the total water lost by the infant, without weighing the infant. In this regard, a collection bag 77 (FIG. 10) may be coupled to the helmet 50 and suit 15 for collecting the water.

In the embodiment being described, the controls 62 and 68 may be coupled to sensors 63 and 65, respectively, for sensing the internal temperature and humidity inside the environment 52 and suit 15. The sensors 63 and 65 may be situated inside the helmet 50 and suit 15, respectively, or coupled directly to the infant's head and body.

In the embodiment being described, the controls 62 and 68 may each include a heating or cooling coil (not shown) and a pump (not shown) for pumping the fluid across the coil to effect controlling the temperature of the fluid before it enters the environment 52 or suit 15. In this regard, if either the predetermined body temperature and predetermined helmet temperatures are selected to be greater than or equal to 0° C., water (i.e., $H_2O$) may be used as the fluid, whereas for temperature less than 0° C., gas may be used as the fluid.

Once the fluid is selected, the pump in controls 62 and 68 pumps the fluid past the coil to effect heating or cooling the fluid before it is pumped into environment 52 and helmet 15 in order to achieve the predetermined helmet temperature and predetermined body temperature, respectively.

It has been found that mainly cold fluid which has to be pumped through as the fluid is easier to obtain from a reservoir than, for example, cooling with air which has a low heat/cold carrying capacity.

Alternatively, controls 62 and 68 may include other means for heating the fluids. Such means may include electrically powered heating devices (not shown), such as resistors (not shown) flown through by current, wrapped around a heat exchanger (not shown) and from outside the actual fluid system going through to the patient (i.e., externally) to heat or cool the fluid (gas or liquid). For achieving cooling, a reservoir (not shown) of iced cubes through which the fluid or the lines 58 and 69, for example, may pass to effect cooling the fluid.

Below 0° C. it is preferable to use alcohols as mentioned earlier. Cooled alcohols down to −30° C. may be pumped from a reservoir through the tubings by a roler pump. For long term cooling or usage of alcohols, a refrigerator device may be required.

Although not shown, the features of control device 36 shown in the embodiment of FIG. 5 could be used with this embodiment such that the fluid which is heated or cooled to the predetermined helmet temperature, for example, is provided to the channels 32 in order to, for example, cool the infant's head.

Also, note that the helmet 50 is portable and separable from the suit 15 so that it can be used independently therefrom. This permits the helmet 50 alone to be used in combination with a traditional incubator. For example, the helmet 57 shown in FIG. 11 may simply be situated around the infant's head to effect climate control, while the infant is in an incubator.

The process utilized by system controller 74 for selectively and independently controlling the temperatures of the infant's head and body will now be described relative to FIG. 9 where the process begins by situating the infant in the body suit 15 (FIG. 7) and placing the helmet 50 over the infant's head, such that the elastic band 54a mates with the collar 15a as shown in FIG. 7 (block 100 in FIG. 8).

At block 102, the user adjusts the body temperature control 72 and body pressure control 70 to the desired predetermined body temperature and a predetermined body pressure/flow, respectively. Likewise, at block 104 the user uses the helmet temperature control 66 and helmet pressure control 64 to set the temperature and pressure/flow of the environment 52 inside helmet 50 to the predetermined helmet temperature and predetermined helmet pressure, respectively.

The process continues at block 106 where the body temperature control 68 continuously monitors and senses the temperature inside suit 15 using sensor 65 and adjusts the temperature of the fluid supplied through inlet tube 69 in response thereto. At decision block 108, it is determined whether the actual body temperature of the infant is within a predetermined tolerance range of the predetermined body temperature. If it is not, then the routine proceeds to block 110 where the body temperature control 68 adjusts the temperature of the fluid supplied through inlet line 69 (FIG. 7). Thereafter, the routine loops back to block 106, as shown.

If the decision at decision block 108 is yes, then the routine proceeds to sense the actual temperature in area 52 using sensor 63 (block 111). The routine then proceeds to decision block 112 where it is determined if the actual helmet temperature is within a predetermined tolerance range of the predetermined helmet temperature. If it is not, then the routine proceeds to block 113 where the helmet temperature 66 adjusts the temperature of the fluid supplied through inlet line 58 in response thereto. Thereafter, the routine loops back to block 111 as shown.

If the decision at decision block 112 is affirmative, then system controller 74 or a user may determine (decision block 114) if the cooling period is complete. If it is not, then the routine proceeds to decision block 116 where it is determined whether it is desired to adjust the predetermined helmet temperature and predetermined body temperature. If it is, then the routine loops back to block 102. Otherwise, the routine proceeds to block 106, as shown.

If the decision at decision block 114 is affirmative, then the infant is removed from the body suit 15 and helmet 50 (block 118) and the procedure terminates.

It should be appreciated that the helmet temperature control 62 and body temperature control 68 are each capable of heating the fluid supplied to inlet lines 58 and 69 to the predetermined helmet temperature and predetermined body temperature, respectively. Alternatively, if it is desired to adjust these temperatures quickly, then the user can adjust the helmet temperature control 62 and body temperature control 68 which substantially simultaneously causes the temperature of the gas supplied to the area 52 of helmet 50 or inside the suit 15 to change very quickly, such as less than about 60 seconds.

In the embodiment being described, the predetermined body temperature may be set to about 35–38° C., while the predetermined helmet temperature is set to about 3° C. less (i.e., 32–35° C.). This facilitates ensuring that the temperature of the infant's head is at least about 2° C.–3° C. lower than the temperature of the infant's body. Thus, advantageously, this system and method provide means for cooling the infant's head, without cooling the infant's body and/or warming the infant's body, without warming the infant's head.

It should be appreciated that the actual helmet temperature and actual body temperature sensed at blocks 111 and 106 (FIG. 9), respectively, correlates directly with the temperature of the infant's head and body, respectively. Alternatively, and as alluded to earlier herein, actual sensed measurements of the temperature of the infant's head and temperature of the infant's body may also be provided, for example, using temperature probes, such as the probes 30 described earlier herein relative to FIG. 4. Although not shown, the temperature probes 30 may be situated on the infant's body, appendages and head and coupled directly to the body temperature control 68 and helmet temperature control 62 for providing real-time, actual temperature feedback information to the body temperature control 68 and helmet temperature control 62. Of course, it is envisioned that other means may also be provided for sensing the temperatures in either the areas inside the suit 15 and helmet 50 or the actual temperature of the infant's body and head for use in controlling the temperature of the gas supplied by the helmet temperature control 62 and body temperature control 68.

It should be appreciated that the features of this invention may be used with all infants and, particularly, for newborn infants. Also, features from the previous embodiments, such as the recess 11 and cover 12 described earlier relative to FIGS. 1A–1C may be combined with the features described relative to FIGS. 7–11. In this regard, on the rear side of the suit 15 an opening (not shown), preferably a closable opening, may be provided via which the excretions of the infants are voided and may be quickly and simply removed by a nurse. In order to prevent excrements from getting inside the suit 15, the suit 15 may also be provided with an adhesive tape (not shown) on the inner side of the opening (not shown). The opening may either expose the anal or both anal and genital regions. This opening may be either formed such that it can be opened/closed by a flap (not shown). Through this opening, a fleece or napkin located in the suit 15 may be removed or replaced or it may be covered by means of a fleece covered sheet, or such that by way of this opening the body region in which excretions are effected is more or less shifted out of the suit.

As alluded to earlier herein, the helmet 50 (FIGS. 7, 8 and 10) may be of a shape such that it snuggle fits the infant's head, is shaped similar to a box as shown in FIG. 11, or snugly fits the infant's neck (FIGS. 7 and 8), without hindering blood flow and breathing, while still permitting cooling of the blood vessels supplying the brain.

The helmet 50 may also be further equipped to secure means, such as tubing, in an infant's nasal passages to facilitate cooling the infant's brain which is located above the nasal passages.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A climate controlled infant suit for independently regulating the climate of a part of an infant, comprising:

a cover for enclosing said part of said infant's body; said cover comprising an impermeable material which is impermeable to an outside environment and enclosing the infant; thereby preventing evaporation from the infant from leaving said suit, thereby creating a vaporized and humidified climate inside said suit;

said cover comprising means for collecting evaporated water for permitting establishment of a water balance without weighing the infant; and a climate control coupled to said cover for independently controlling a temperature inside said suit; said climate control maintaining said temperature inside said suit at a predetermined temperature, without introducing heated or cooled water vapor into said cover.

2. The climate-controlled infant suit as recited in claim 1 wherein said predetermined temperature comprises a predetermined helmet temperature corresponding to a temperature around said infant's head and a predetermined body temperature corresponding to a temperature around said infant's body, wherein said predetermined helmet temperature is lower than said predetermined body temperature.

3. The climate-controlled infant suit as recited in claim 1 wherein said cover comprises a helmet portion and a body portion, said climate control comprises a helmet temperature control coupled to said helmet portion and a body temperature control coupled to said body portion.

4. The climate-controlled infant suit as recited in claim 1 wherein said cover comprises a body portion and a helmet portion, said climate control comprises a helmet temperature control coupled to the helmet portion and a body temperature control coupled to said body portion; said temperature control further comprising a plurality of sensors for sensing actual temperatures in said body area and said helmet area; said helmet temperature control and said body temperature control adjusting a temperature of a fluid in order to maintain said predetermined body temperature and predetermined head temperature in response to said actual temperatures.

5. The suit as recited in claim 1 wherein said climate control utilizes less than about 3 Watt per Kg body mass for a time period of 1 hour to control the climate associated with said head or body to normal values (35° to 38°) in an ambient temperature (15° C. to 25° C.) room.

6. The suit as recited in claim 1 wherein said cover comprises an open-faced helmet.

7. The suit as recited in claim 1 wherein said cover comprises a helmet having a lid which can be moved from an open to a closed position.

8. The suit as recited in claim 1 wherein said means comprises a bag.

9. The climate controlled infant suit as recited in claim 1 wherein said cover comprises a rump part for receiving an infant's rump, tubular arm parts for receiving an infant's arms, tubular leg parts for receiving an infant's legs and a helmet part for receiving an infant's head, said rump part, said tubular arm parts, said tubular leg parts and said helmet part being sewn together to prevent said evaporation.

10. The climate controlled infant suit as recited in claim 9, wherein at least one of said tubular arm parts or said tubular leg parts may be rolled up or opened to expose at least one of an infant's arms while maintaining the climate inside said suit.

11. A system for independently regulating a temperature of an infant's head and body comprising:

a cover for situating over a part of the infant;

said cover enclosing said part of said infants body; said cover comprising an impermeable material which is impermeable to an outside environment and enclosing the infant thereby preventing evaporation from the infant from leaving said suit, thereby creating a vaporized and humidified climate inside said suit;

said cover comprising a collector for collecting evaporated water for permitting establishment of a water balance without weighing said infant; and means coupled to said cover for selectively and independently controlling a temperature of said climate inside said cover to control the temperature of said infant's head and body, without introducing heated or cooled water vapor into said cover.

12. The system as recited in claim 11 wherein said cover is situated over both said head and said body, said means further comprising:
a temperature controller coupled to said cover; said temperature controller being capable of providing a temperature-controlled fluid (liquids and gases) to said cover in order to maintain the temperature associated with said head at a predetermined head temperature and a temperature associated with said body at a predetermined body temperature.

13. The system as recited in claim 6 wherein said predetermined helmet temperature is lower than said predetermined body temperature.

14. The system as recited in claim 12 wherein said temperature controller comprises at least one sensor associated with said cover for sensing an actual head temperature.

15. The system as recited in claim 6 wherein said temperature controller comprises a plurality of sensors coupled to said infant's body and head for sensing an actual temperature of said body and said head, respectively.

16. The system as recited in claim 11 wherein said collector is a bag.

17. The system as recited in claim 11 wherein said collector is a bag and a tube coupled to said cover.

18. A method for independently regulating a climate around an infant, comprising the steps of:
establishing a predetermined temperature for a plurality of regions of the infant;
placing at least a part of said infant in a cover comprising an impermeable material that is impermeable to an outside environment to permit evaporation from the infant to be gathered;
regulating the climate inside said cover such that actual temperatures of said infant's head are lower than actual temperatures of said infant's body, without introducing heated or cooled water vapor into said cove; and
collecting evaporation from the infant to measure a water balance without weighing the infant.

19. The climate controlled infant suit as recited in claim 18 wherein said cover comprises a rump part for receiving an infant's rump, tubular arm parts for receiving an infant's arms, tubular leg parts for receiving an infant's legs and a helmet Dart for receiving an infant's head, said rump part, said tubular arm parts, said tubular leg parts and said helmet part being sewn together to prevent said evaporation.

20. A method for independently regulating a climate around an infant, comprising the steps of:
establishing a predetermined temperature for a plurality of regions of the infant;
placing at least a part of said infant in a cover comprising an impermeable material that is impermeable to an outside environment to permit evaporation from the infant to be gathered;
regulating the climate inside said cover such that actual temperatures of said infants head are lower than actual temperatures of said infant's body; and
establishing a predetermined head temperature for said head to be lower than a predetermined body temperature for said body.

21. A method for independently regulating a climate around an infant, comprising the steps of;
establishing a predetermined temperature for a plurality of regions of the infant;
placing at least a part of said infant in a cover comprising an impermeable material that is impermeable to an outside environment to permit evaporation from the infant to be gathered:
regulating the climate inside said cover such that actual temperatures of said infant's head are lower than actual temperatures of said infant's body; and
establishing said predetermined head temperature to be between at least 1°–3° C. lower than said predetermined body temperature.

22. A climate controlled infant suit for independently regulating a climate around a part of an infant, comprising a head and a body, comprising:
a cover for covering at least a portion of the infant, said cover comprising an impermeable material to prevent evaporation from the infant's suit; and
a climate control coupled to said cover for independently controlling said climate so that at least a head temperature associated with said infant's head is maintained a predetermined temperature without introducing heated or cooled water vapor into said cover;
wherein said cover defines an environment/climate for receiving at least a portion of said infant such that an airspace between said cover and said infant defines a volume of less than 1.0 liter per Kg body weight of the infant to which the suit is applied;
said climate control using less than 3 watt per Kg body mass of said infant to maintain said predetermined temperature at approximately ambient temperature;
said cover comprising a collector for collecting evaporated water for permitting establishment of a water balance without weighing said infant.

23. The climate controlled infant suit as recited in claim 22 wherein said cover comprises a rump part for receiving an infant's rump, tubular arm parts for receiving an infant's arms, tubular leg parts for receiving an infant's legs and a helmet part for receiving an infant's head, said rump part, said tubular arm parts, said tubular leg parts and said helmet part being sewn tether to prevent said evaporation.

24. A temperature controlled infant suit for use with an infant comprising a head and a body, said suit comprising:
a body portion defining a body area for receiving a body of an infant;
a helmet portion defining a helmet area for receiving a head of the infant; said body and helmet portions providing a cover comprising an impermeable material which is impermeable to an outside environment and which encloses the infant to prevent evaporation from the infant from leaving said suit, thereby creating a vaporized and humidified climate inside said suit; and
a climate control coupled to said body portion and said helmet portion for selectively controlling a temperature of said climate in said body area and said helmet area, thereby controlling a body temperature of said infants body and a head temperature of said infant's head, without introducing heated or cooled water vapor into said cover; and
said cover comprising a collector for collecting evaporated water for permitting establishment of a water balance without weighing said infant.

25. The temperature-controlled infant suit as recited in claim 24 wherein said climate control causes said body temperature associated with said body portion to be maintained at a predetermined body temperature and said head temperature inside a helmet area to be maintained at a predetermined helmet temperature, wherein said head temperature is lower than said predetermined body temperature.

26. The temperature-controlled infant suit as recited in claim 24 wherein said climate control comprises a helmet temperature control coupled to said helmet portion, said helmet temperature control controlling a temperature of said infant's head.

27. The climate controlled infant suit as recited in claim 2 wherein said cover comprises a body portion defining a body area and a helmet portion defining a helmet area said climate control comprises a helmet temperature control coupled to said helmet portion, and a body temperature control coupled to said body portion; said climate control further comprising a plurality of sensors for sensing actual temperatures in said body area and said helmet area; said helmet temperature control and said body temperature control adjusting a temperature of said climate in said suit in order to maintain a predetermined body temperature of said infant and a predetermined head temperature of said infant in response to said actual temperatures.

28. The climate controlled infant suit as recited in claim 24 wherein said cover comprises a rump part for receiving an infant's rump, tubular arm parts for receiving an infant's arms, tubular leg parts for receiving an infant's legs and a helmet part for receiving an infant's head, said rump part, said tubular arm parts, said tubular leg parts and said helmet part being sewn together to prevent said evaporation.

\* \* \* \* \*